(12) United States Patent
Chao et al.

(10) Patent No.: US 6,221,396 B1
(45) Date of Patent: Apr. 24, 2001

(54) ORAL CISAPRIDE DOSAGE FORMS WITH AN EXTENDED DURATION

(75) Inventors: Shouchung Chao; Wen-Pao Tseng; Hui-Fang Chang; David Chen; Shu-Bin Lu, all of Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 09/349,034

(22) Filed: Jul. 7, 1999

(30) Foreign Application Priority Data

Jul. 17, 1998 (CN) .................................. 87111676

(51) Int. Cl.⁷ .............................. A61K 9/32; A61K 9/28; A61K 9/16
(52) U.S. Cl. ...................... 424/482; 424/474; 424/490; 424/494; 424/497
(58) Field of Search .................... 424/464, 468, 424/474, 480, 482, 489, 490, 494, 497

(56) References Cited

U.S. PATENT DOCUMENTS

| | | | |
|---|---|---|---|
| 3,845,770 | 11/1974 | Theeuwes et al. | 128/260 |
| 3,916,889 | 11/1975 | Russell | 128/145.8 |
| 4,063,064 | 12/1977 | Saunders et al. | 219/121 L |
| 4,088,864 | 5/1978 | Theeuwes et al. | 219/121 LM |
| 4,962,115 | 10/1990 | Van Daele | 514/326 |
| 5,582,837 | 12/1996 | Shell | 424/451 |
| 5,646,131 | 7/1997 | Badwan et al. | 514/58 |
| 5,885,616 | 3/1999 | Hsiao et al. | 424/472 |
| 5,897,910 * | 4/1999 | Rosenberg et al. | 427/2.14 |
| 6,030,988 * | 2/2000 | Gilis et al. | 514/327 |

FOREIGN PATENT DOCUMENTS

| | | |
|---|---|---|
| 0076530 | 4/1983 | (EP) . |
| 9614070 | 5/1996 | (WO) . |
| 9829095 | 7/1998 | (WO) . |

* cited by examiner

Primary Examiner—Thurman K. Page
Assistant Examiner—S. Tran
(74) Attorney, Agent, or Firm—Ladas & Parry

(57) ABSTRACT

The present invention provides sustained release oral solid dosage forms of cisapride by using a multi-particulate system, which are bioavailable and can provide efficient blood level of cisapride over 24 hours. Unit dosage forms of cisapride which comprise a plurality of substrates containing sustained release cisapride, as well as pharmaceutical compositions containing the dosage forms, are also disclosed herein.

25 Claims, No Drawings

ORAL CISAPRIDE DOSAGE FORMS WITH AN EXTENDED DURATION

BACKGROUND OF THE INVENTION

1. Field of the Invention

The present invention relates to bioavailable sustained release cisapride formulations which provide an extended duration of effect when orally administered.

2. Description of Related Prior Art

Formulations which can provide sustained release (slow release) of pharmacologically active substances when administrated orally to humans or animals are well-known in the pharmaceutical art. A sustained release formulation is used to delay absorption of an active substance until it has reached a desired area in the gastrointestinal tract. Sustained release preparations provide a longer period of the drug substances in blood after the administration of the substance than traditional rapid release dosage forms.

EP 0076530 A2 and U.S. Pat. No. 4,962,115 disclose cisapride, i.e., (±)-cis-4-amino-5-chloro-N-1-[3-(4-fluorophenoxy)propyl]-3-methoxy-4-piperidine-2-methoxybenzamide monohydrate, as a gastroenterokinetic promoter and the synthesis thereof, which are incorporated herein by reference. Cisapride has two enantiomers consisting of (+)-cisapride and (−)-cisapride. Cisapride is known to be able to enhance the propelling activity of esophagus, increase the tensile force of lower esophageal sphincter, and promote the gastrointestinal emptying. With respect to therapeutic applications, cisapride can be used in therapy of a variety of diseases associated with gastroenterokinesia (such as reflective reflux of esophagus, anorexia, nausea and emesis), gastroparesis resulted from neurectomy and vagal neurectomy, pseudo-ileus and chronic constipation. The pharmacological mechanism of cisapride is mainly involved in stimulating plexus myentericus to enhance physiological secretion of acetylcholine.

There are many inherent advantages on the development of long-term effective sustained release formulations. Among the advantages, sustained release dosage forms increase the compliance of patients. It is more convenient for patients to receive long-term effective sustained release cisapride dosage forms once or twice a day than the conventional cisapride dosage forms administered four times a day. Another advantage of sustained release formulations is to greatly reduce various adverse side effects caused by drug administration. A desired modulation of local or systemic drug concentrations in patients would be resulted from the slow release of the sustained release dosage forms. Appropriate modulation of the adverse effects upon administering conventional cisapride dosage forms, such as diarrhea and colic, can be alleviated to a great extent.

A major issue during the development of a sustained release cisapride dosage form was how to overcome the problem of the solubility of cisapride. It is known in the art that a better solubility of cisapride was observed under acidic conditions, while a very poor solubility, almost insoluble, in a pH condition near neutral (i.e., the pH of intestinal fluid) was observed. A good sustained release dosage form should meet the goal to allow an appropriate amount of a drug substance sustained-release in every area of the gastrointestinal tract. The major technical concerns during developing a cisapride sustained release dosage form focus on a possible solution to the existing problem that an effective level of drug in the blood cannot be maintained for a long period. The dissolution of cisapride in a neutral pH condition in the intestinal tract is so poor as not to allow cisapride persistently released in an adequate amount.

There are a number of techniques for promoting solubility and dissolution of drugs. For example, U.S. Pat. No. 5,646,131 describes a method for the solubility improvement of water insoluble or almost insoluble drugs where a composition comprising a cyclodextrin, a carboxylic acid and a drug was provided to enhance the solubility of the drug or its complex.

U.S. Pat. No. 5,582,837 discloses a formulation capable of increasing the residence time in the stomach in view of the feature of cisapride (good solubility the stomach) to provide a resolution to the little solubility in the intestine. The prior formulation was a drug composition in the tablet or capsule form including hydroxyethylcellulose, hydroxypropylcellulose, and the like. The drug composition would be disintegrated into small particulates in the stomach. The particulates absorb water and swell to form hydrogel-like materials which can extend the residence time in the stomach such that the slow-release effect can be achieved.

WO 96/14070 describes a method of improving the solubility of cisapride by forming a cisapride-(L)-tartrate from cisapride and tartaric acid. A sustained release tablet comprising hydroxypropylmethylcellulose with high viscosity (e.g., 15000 mPa.s) and the thus-formed cisapride-(L)-tartrate was also provided in WO 96/14070. Hydroxypropylmethylcellulose with high molecular weight would form a hydrogel in water to achieve slow release of cisapride.

All of the literature references and publications as mentioned herein are incorporated by reference.

The prior approaches, such as a complex of cyclodextrin and cisapride or a salt of tartaric acid and cisapride, may enhance the solubility of cisapride in the stomach to some extent. However, the problem resulted from the pharmacokinetic profile of cisapride (i.e., good solubility in an acidic environment, while poor solubility in a neutral or basic environment) has not been resolved yet. Furthermore, whether the pharmacodynamic properties of the prior cisapride complex or salt are comparable to cisapride still needs to undergo time-consuming and expensive experiments.

Therefore, there is a need in the art for a long-term effective cisapride formulation, such as suitable for once- or twice-a-day administration, which would be more convenient for administration to patients. The formulation would be expected to have enhanced solubility in the intestinal tract and retain the pharmacodynamic characteristics of cisapride.

SUMMARY OF THE INVENTION

An objective of the present invention is to provide an oral pharmaceutical dosage form of cisapride, which is suitable for once- or twice-a-day administration.

Another objective of the present invention is to provide a sustained release cisapride preparation which is bioavailable and can provide a patient an effective steady-state blood level for longer than 12 hours, preferably at least 24 hours.

Another objective of the present invention is to provide a method for treating a patient with an oral cisapride dosage form which is bioavailable and can provide a desired effective period of longer than 12 hours, preferably at least 24 hours.

More particularly, yet another objective of the present invention is to provide a once-a-day oral sustained release cisapride dosage form, which comprises a plurality of pharmaceutically acceptable substrates in a unit dosage. The unit dosage of the substrates comprise an effective amount of cisapride. The unit dosage is bioavailable and provides an effective blood level of cisapride for at least 24 hours. The unit dosage of the substrates, for example, can be encapsulated within a hard gelatin capsule for oral administration.

The present invention further relates to a bioavailable sustained release cisapride dosage form which comprises pharmaceutically acceptable substrates coated with one or more layers comprising an effective amount of cisapride and one or more enteric polymers. The enteric polymer is selected from the group consisting of:
(i) an enteric acrylic polymer, such as copolymer of methyl methacrylate and methacrylic acid;
(ii) a phthalic acid derivative of vinyl polymer or copolymer, such as copolymers of vinyl alcohol, vinyl acetate and vinyl phthalate; and
(iii) a phthalic acid derivative of cellulose, such as hydroxypropylmethyl cellulose phthalate or cellulose acetate phthalate.

The dosage form according to the present invention is capable of providing a sustained release of cisapride in an aqueous medium at least 24 hours.

The present invention further relates to a bioavailable sustained release cisapride dosage form which comprises the pharmaceutically acceptable substrates coated with an effective amount of cisapride and enteric polymers. The substrates further comprise a sustained release outer film which comprising an effective amount of one or more hydrophobic substances. The hydrophobic substance is selected from the group consisting of:
(i) an acrylic polymer, such as methacrylic acid copolymer (e.g., copolymer of methyl methacrylate and methacrylic acid, or copolymer of ethyl acrylate and methacrylic acid), or copolymer of ethyl acrylate, methyl methacrylate and chlorinated trimethylaminoethyl methacrylate; and
(ii) an alkyl cellulose, such as ethyl cellulose.

The dosage form according to the present invention is capable of providing a sustained release of cisapride in an aqueous medium for at least 24 hours.

The present invention further relates to a bioavailable sustained release cisapride composition, comprising:
(i) the pharmaceutically acceptable substrates coated with an effective amount of cisapride and one or more above-mentioned enteric polymers, as well as the above-mentioned hydrophobic outer film; and
(ii) one or more of the pharmaceutically acceptable substrates coated with an effective amount of cisapride and one or more above-mentioned enteric polymers.

The present invention further relates to a bioavailable sustained release cisapride dosage form which comprises the pharmacologically acceptable substrates coated with an effective amount of cisapride, one or more above-mentioned enteric polymers, and the above-mentioned hydrophobic outer film. The substrates further include one or more layers of overcoats each containing an effective amount of cisapride and one or more above-mentioned enteric polymers.

Thus, another objective of the present invention is to provide a pharmaceutical composition containing one or more dosages forms as defined herein.

The term "enteric" is defined for the purposes of the present invention as a substance which is insoluble at a pH value of less than 4.5 and is soluble at a pH value of greater than 5.5.

The term "bioavailability" or "bioavailable" is defined for the purposes of the present invention as the extent to which cisapride is absorbed from the unit dosage forms and becomes available at the action site of cisapride.

The term "sustained release" is defined for the purposes of the present invention as the release of cisapride at such a rate that blood (e.g., plasma) levels are maintained within the therapeutic range but below toxic levels over a period of time of about 12 hours or longer, preferably, about 24 hours or longer.

The term "substrate" is defined for the purposes of the present invention as spheres, beads, microspheres, seeds, pellets, ion-exchange resin beads, and other multi-particulate system containing cisapride, having a diameter of from about 0.1 mm to about 3 mm, and preferably between 0.5 mm and 2.0 mm.

The term "unit dosage" is defined for the purposes of the present invention as the total amount of the substrates required for administering a desired dosage of cisapride to a patient.

The sustained release substrates according to the present invention permits the release of cisapride in an aqueous medium over an extended period. The term "aqueous medium" is defined for the purposes of the present invention as any pharmacologically acceptable aqueous solvent medium, gastric fluid and/or intestinal fluid.

DETAILED DESCRIPTION OF THE INVENTION

The present invention discloses unique and novel formulations which release cisapride slowly and uniformly in the gastrointestinal tract. The sustained release dosage form according to the present invention in particular characterized by slow release cisapride substrates can overcome the problem of the poor solubility of cisapride under a neutral condition and permit a sustained release of cisapride in an appropriate amount in the intestinal fluid.

The sustained release formulation according to the present invention can be used in combination with any multi-particulate system (substrates), such as, beads, spheres, microspheres, seeds, pellets, ion-exchange resin beads, and others by which a sustained release of cisapride can be achieved. The beads, particulates, spheres, or pellets prepared according to the present invention may be formulated in a capsule or any other suitable unit dosage forms.

When the substrates according to the present invention are pharmaceutical beads, the beads are of a size of 8 to 50 mesh. In a specific preferred embodiment, the beads are, for example, Nu-pareil® 25/35 beads (Ingredient Tech).

In a preferred embodiment, the sustained release cisapride dosage form according to the present invention comprises a multiplicity of substrates containing the active ingredients, which substrates are coated with sustained release coatings. The coating formulation according to the present invention can be used to provide a tough film which is smooth, non-toxic and non-sticky, and can support pigments and other coating additives.

In an embodiment, the present invention provides a once- or twice-a-day bioavailable sustained release cisapride dosage form which comprises pharmaceutically acceptable substrates coated with one or more layers comprising an effective amount of cisapride and one or more enteric polymers. The enteric polymers are selected from the group consisting of:
(i) an enteric acrylic polymer, such as copolymer of methyl methacrylate and methacrylic acid;
(ii) a phthalic acid derivative of vinyl polymer or copolymer, such as copolymers of vinyl alcohol, vinyl acetate and vinyl phthalate; and
(iii) a phthalic acid derivative of cellulose, such as hydroxypropylmethylcellulose phthalate and cellulose acetate phthalate.

The dosage form according to the present invention is to provide a sustained release of cisapride in an aqueous medium for at least 24 hours.

In a further embodiment, the present invention provides a once- or twice-a-day bioavailable sustained release cisapride dosage form which comprises pharmacologically acceptable substrates coated with an effective amount of cisapride and one or more above-mentioned enteric polymers. The substrates further comprise a sustained release outer film that contains an effective amount of one or more hydrophobic substances. The hydrophobic substance is selected from the group consisting of:

(i) an acrylic polymer, such as a methacrylic acid copolymer (e.g., a copolymer of methyl methacrylate and methacrylic acid, or a copolymer of ethyl acrylate and methacrylic acid), or a copolymer of ethyl acrylate, methyl methacrylate and chlorinated trimethylaminoethyl methacrylate; and (ii) an alkyl cellulose, such as ethyl cellulose.

The dosage form according to the present invention is to provide a sustained release of cisapride in an aqueous medium for at least 24 hours.

In a further embodiment, the present invention provides a bioavailable sustained release cisapride composition, comprising:

(i) the pharmacologically acceptable substrates coated with an effective amount of cisapride and one or more above-mentioned enteric polymers, as well as the above-mentioned hydrophobic outer film; and (ii) the pharmacologically acceptable substrates coated with an effective amount of cisapride and one or more above-mentioned enteric polymers.

In a further embodiment, the present invention provides a once- or twice-a-day bioavailable sustained release cisapride composition which comprises the pharmaceutically acceptable beads coated with an effective amount of cisapride, one or more above-mentioned enteric polymers, the above-mentioned hydrophobic outer film and one or more layers of overcoats each containing an effective amount of cisapride and one or more above-mentioned enteric polymers.

The solvents for the enteric polymers or hydrophobic substances which may be used in the present invention are any pharmaceutically acceptable solvents including water, methanol, ethanol, acetone, methylene chloride and mixtures thereof Preferably, both cisapride and the enteric polymers can be dissolved together in an organic solvent or its mixture with water, and the outer film is a hydrophobic substance based on an aqueous dispersion.

The enteric polymer or hydrophobic substance contained in the sustained release coating may be a pharmaceutically acceptable acrylic polymer including, but not limited to, copolymer of methacrylic acid and methyl methacrylate, copolymer of methacrylic acid and ethyl acrylate, copolymer of ethoxyethyl methacrylate, cyanoethyl methacrylate and aminoalkyl methacrylate, poly(acrylic acid), poly(methacrylic acid), methacrylic acid alkyl amide copolymer, poly(methyl methacrylate), polymethacrylate, polyacrylamide, aminoalkyl methacrylate copolymer, poly(methacrylic acid anhydride), and dehydrated methacrylate copolymer.

In a preferred embodiment, the acrylic polymers are one or more amino-methacrylate copolymers which are well known in the art.

The acrylic polymer may be an acrylic resin varnish in an aqueous dispersion, for example, Eudragit® commercially available from Rohm Pharma. In a preferred embodiment, the acrylic polymer is Eudragit® L available from Rohm Pharma. In a further preferred embodiment, the acrylic coating may be Eudragit® RL30D or RS30D, preferably Eudragit® RL30D. Eudragit® RL30D is a copolymer of acrylates and methacrylates containing lower content of quaternary amino groups, wherein the mole ratio of amino groups to the residual neutral (meth)acrylates is 1:20 and its average molecular weight is about 150,000. Certainly, persons skilled in the art can understand that other acrylic polymers may be used as well.

In other preferred embodiments, the enteric polymer was a phthalic acid derivative of cellulose and the hydrophobic substance was an alkyl cellulose, such as ethyl cellulose. The ethyl cellulose used in the present invention may be Ethocel®(Dow). Persons skilled in the art will understand that other alkyl cellulose can be used to replace (or in combination with) ethyl cellulose as the hydrophobic substance according to the present invention.

The phthalic acid derivatives of cellulose used in the present invention may be hydroxypropylmethyl cellulose phthalate. In a preferred embodiment, the hydroxypropylmethyl cellulose phthalate used in the present invention is HPMCP®(Shin Etsu K.K., Japan). The phthalic acid derivatives of cellulose used for the purposes of the present invention further include cellulose acetate phthalate.

The enteric polymer used for the purposes of the present invention may be phthalic acid derivatives of vinyl polymer or copolymer, such as copolymer of vinyl alcohol, vinyl acetate and vinyl phthalate. In a preferred embodiment, such copolymer of vinyl alcohol, vinyl acetate and vinyl phthalate is Opadry® (Colorcon).

According to the present invention, the once- or twice-a-day bioavailable sustained release cisapride dosage form has a weight ratio of cisapride to the enteric polymer which is generally between about 10:1 and about 1:10, preferably between about 5:1 and about 1:5 and more preferably, between about 2:1 and about 1:2.

According to the present invention, the once- or twice-a-day bioavailable sustained release cisapride dosage form has about 1% to about 30%, preferably about 1% to about 20%, and more preferably about 1% to about 10% of the hydrophobic outer film, based on the weight of the cisapride dosage form.

In a preferred embodiment according to the present invention, the coating includes an aqueous dispersion of a hydrophobic substance. An effective amount of a plasticizer may be incorporated into the aqueous dispersion of the hydrophobic substance for improving the physical properties of the outer film. For example, since ethyl cellulose has a relatively high glass transition temperature where a flexible film under normal coating conditions cannot form, ethyl cellulose must be softened prior to its use as the coating material. In general, the amount of the plasticizer used in the coating solution depends on that of the components forming the film, for example, the amount of the plasticizer used according to the present invention is from 1% to 30% by weight of the components forming the film. However, a required exact concentration of the plasticizer should be determined through careful experiments.

Suitable plasticizers for ethyl cellulose include the non-water-soluble plasticizers, such as dibutyl sebacate, diethyl phthalate diacetate, triethyl citrate, tributyl citrate, and triacetin. Other non-water-soluble plasticizers (e.g., ricinus oil) may be used. The triethyl citrate is particularly preferred.

Suitable plasticizers for the acrylic polymers used in the present invention includes, for example, triethyl citrate, tributyl citrate, dibutyl orthophthalate, 1,2-propylene glycol, polyethylene glycol, propylene glycol, diethyl phthalate diacetate, ricinus oil and triacetin. Other non-water-soluble plasticizers (e.g., ricinus oil) may be used. The triethyl citrate is particularly preferred.

The sustained release properties of the formulations according to the present invention can be modified, for example, by changing thickness of the hydrophobic coating, changing specific hydrophobic substances, changing relative amounts of, for example, different acrylic varnishs, changing the way the plasticizers are incorporated (if the sustained release coating is derived from an aqueous dispersion of a hydrophobic substance), changing the relative amounts of the plasticizers to the hydrophobic substances, adding an additional component, changing producing processes, and the like.

The sustained release spheres or beads coating with cisapride and polymers according to the present invention can be prepared by, for example, co-dissolving cisapride and suitable polymers in an organic solvent and then spraying the solution onto a substrate, such as Nu-pareil®25/35 beads, using a Wurster Insert. Optionally, additional ingredients are also added prior to coating the beads in order to assist cisapride binding to the substrates, to color the solution and/or to enhance solubility of cisapride after administration, etc. For example, a product including hydroxypropyl cellulose or hydroxypropyl methylcellulose, ethyl cellulose, etc. with or without surfactant (such as Tween 80 or sodium lauryl sulfate) and/or colorant may be added to the solution, and the solution mixed prior to application of the same onto beads. The resultant coated substrate, in this example beads, may then be optionally overcoated with a barrier agent, to separate cisapride from the hydrophobic sustained release coating. An example of a suitable barrier agent is one which comprises hydroxypropyl methylcellulose. However, any film-former known in the art may be used. It is preferred that the barrier agent does not affect the dissolution rate of the final product.

The cisapride substrates according to this invention may be overcoated with a hydrophobic substance, preferably with an effective amount of plasticizer.

In addition to the film-former, the coating solutions used in this invention may contain a plasticizer, a solvent system (e.g., water), an anti-sticking agent (e.g., talc), a colorant, and the like to provide elegance and product distinction. Color may be added to the solution of cisapride and polymer, or in addition to the aqueous dispersion of hydrophobic substance.

By means of any suitable spray equipment known in the art, the plasticized aqueous dispersion of hydrophobic substance may be applied onto the substrate containing cisapride. In a preferred method, a Wurster fluidized-bed system is used wherein an air jet, injected from underneath, fluidizing the core material and effect drying while the acrylic polymer coating is sprayed on. A sufficient amount of the aqueous dispersion of hydrophobic substance to obtain a predetermined sustained release of cisapride when the coated substrate is exposed to aqueous solutions (e.g., intestinal fluid) is preferably applied, taking into account the physical characteristics of cisapride, the manner of incorporation of the plasticizer, etc.

Next, the coated beads are cured to obtain a stabilized release rate of cisapride.

When the coating comprises an aqueous dispersion of ethylcellulose, the coated substrate is preferably subjected curing to at a temperature (e.g., about 60° C.) greater than the glass transition temperature of the coating solution (i.e., ethylcellulose) and at a relative humidity from about 60% to about 100%, until the end-point of curing is reached (at a relative humidity of about 60% to about 100% for a time period from about 48 to about 72 hours).

In preferred embodiments according to the present invention directly to the acrylic coating, a stabilized product is obtained by subjecting the coated substrate to oven curing at a temperature above the glass transition temperature of the plasticized acrylic polymer for the required period of time, the optimum values for temperature and time for the particular formulation being determined experimentally. In certain embodiments of the present invention, the stabilized product is obtained via an oven curing at a temperature of about 45° C. for a time period from about 24 to 48 hours or longer.

The release of cisapride from the sustained release formulation according to the present invention can be adjusted to a desired rate, for example, by adding further one or more release-modifying agent, or by providing one or more passage ways through the coating. The ratio of hydrophobic substance to water soluble material is determined by, inter alia, the required release rate and the solubility characteristics of cisapride.

The release-modifying agents which function as a pore-forming agent may be organic or inorganic, and cover materials that can be dissolved, extracted or leached from the coating in the circumstances of use. The pore-forming agent may comprise one or more hydrophilic substances, such as hydroxypropylmethylcellulose, for example, HPMC® (Shin Etsu K.K., Japan), and the like.

The sustained release coating in the present invention may also include further erosion-promoting agents, for example, starch and gum.

The sustained release coatings of the present invention may also include materials useful for making microporous lamina in the environment of use, such as polycarbonates composed of linear polyesters of carbonic acid where the carbonate groups reoccur in the backbone of the polymer.

The release-modifying agent may include a semi-permeable polymer.

In the preferred embodiments of the present invention, the release-modifying agent is selected from hydroxypropylmethylcellulose, metal salts of stearic acid, and mixtures thereof.

The sustained release coatings of the present invention may also include an exit means, including at least one passageway, orifice or analogues thereof. The passageway can be formed by the methods as those described in U.S. Pat. Nos. 3,845,770, 3,916,889, 4,063,064 and 4,088,864, which are incorporated herein by reference. The passageway can have any shape, such as round, triangular, rectangular, elliptical, irregular shapes, and the like.

In addition to the ingredients as described above, a sustained release matrix may also contain appropriate amounts of other materials commonly used in the pharmaceutical art, such as, diluents, lubricants, binders, granulating aids, colorants, flavorings and glidants.

In certain preferred embodiments of the present invention, an effective amount of cisapride in immediate release form is included in the sustained release unit dose cisapride formulation. The immediate release form of cisapride is included in an amount which is effective to shorten the time to maximum concentration of cisapride in blood (e.g., plasma). By including such an effective amount of immediate release cisapride in the unit dose, patients rapidly receive a considerable therapeutic effect after administration. In such embodiments, an effective amount of cisapride in immediate release form may be coated onto the substrates according to the present invention. For example, the immediate release layer would be overcoated on top of the controlled release coating. It is understood by those skilled in the art that, where a plurality of the sustained release substrates comprising an effective unit dose of cisapride are incorporated into a hard gelatin capsule, the immediate release portion of cisapride dose may be incorporated into the gelatin capsule through inclusion of sufficient amount of immediate release cisapride as a powder or granulate within the capsule. Alternatively, the gelatin capsule itself may be coated with an immediate release layer of cisapride. One skilled in the art will recognized other alternative manners of incorporating the immediate release cisapride portion into the unit dosage.

EXAMPLES

The following examples illustrate various aspects of the the present invention but do not limit the claims in any manner whatsoever.

Example 1

Step 1

40 g of cisapride, 40 g of Eudragit® L(Rohm Pharma, Germany), and 20 g of Tween 80 (Merck) were dissolved in a mixture of 250 ml of methanol and 250 ml of methylene chloride. 60 g of 30–35 mesh beads(Nu-pareil®) were charged in a Wurster Insert of a Glatt equipped with a 1.2 mm spray nozzle. The beads were coated with the mixed solution. Upon completion the beads were cured in a dry oven of 40° C. for 20 hours (yield 97%).

Step 2

6.7 g of Eudragit®RL30D (Rohm Pharma), 0.4 g of HPMC®(Shin Etsu, Japan) and 0.48 g of polyethylene glycol were dissolved in 30 g of water, into which a suitable amount of talc was added. 50 g of the beads from Step 1 were coated with the suspension (99% yield).

Dissolution tests were carried out according to U.S.P. Apparatus II (23rd edition, Paddle Method) in a buffer solution of pH=1.2 (simulated gastric fluid without enzymes) or a buffer solution of pH=7.5 containing 0.2% w/w sodium lauryl sulfate (simulated intestinal fluid without enzymes) at the temperature of 37±0.5° C. at 100 rpm and the UV absorption was measured at the wavelength of 276 nm. The results of the percent of cisapride dissolved in relation to time are set forth below:

|             | % cisapride dissolved | |
| --- | --- | --- |
| Time (hour) | pH = 1.2 | pH = 7.5 |
| 1  | 9  | 19  |
| 2  | 12 | 41  |
| 4  | 16 | 71  |
| 8  | 22 | 98  |
| 16 | 29 | 100 |
| 24 | 34 | 100 |

Example 2

40 g of cisapride, 40 g of Eudragit® L, 20 g of Tween 80 and 17 g of HPMC® were dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 94%).

Products were tested under the same dissolving conditions as employed in Example 1 and the data were as follows:

|             | % cisapride dissolved | |
| --- | --- | --- |
| Time (hour) | pH = 1.2 | pH = 7.5 |
| 1  | 25 | 72  |
| 2  | 32 | 94  |
| 4  | 42 | 95  |
| 8  | 53 | 95  |
| 16 | 66 | 96  |
| 24 | 76 | 100 |

Example 3

40 g of cisapride, 40 g of Eudragit® L and 16 g of HPMC® were co-dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 96%).

Products were tested under the same dissolving conditions as described in Example 1 and the data were as follows:

|             | % cisapride dissolved | |
| --- | --- | --- |
| Time (hour) | pH = 1.2 | pH = 7.5 |
| 1  | 25 | 40  |
| 2  | 31 | 68  |
| 4  | 40 | 91  |
| 8  | 52 | 100 |
| 16 | 67 | 100 |
| 24 | 78 | 100 |

Example 4

12 g of Eudragit® RL30D, 0.86 g of polyethylene glycol and 0.72 g of HPMC® were co-dissolved in a 50 ml of water and a suitable amount of talc was added. The solution was used to coat on the surface of 50 g of the drug-core beads as produced in Example 3 (yield 98%).

Products were tested under the same dissolving conditions as described in Example 1 were as follows:

|             | % cisapride dissolved | |
| --- | --- | --- |
| Time (hour) | pH = 1.2 | pH = 7.5 |
| 1  | 9  | 8  |
| 2  | 16 | 19 |
| 4  | 28 | 29 |
| 8  | 43 | 50 |
| 16 | 61 | 85 |
| 24 | 72 | 95 |

Example 5

40 g of cispride, 40 g of Eudragit® L and 20 g of HPMC® were co-dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 96%).

Products were tested under the same dissolving conditions as described in Example 1 and the data were as follows:

|          | % cisapride dissolved | |
| Time (hour) | pH = 1.2 | pH = 7.5 |
| --- | --- | --- |
| 1 | 28 | 11 |
| 2 | 31 | 28 |
| 4 | 34 | 71 |
| 8 | 39 | 89 |
| 16 | 46 | 97 |
| 24 | 51 | 99 |

Example 6

40 cisapride, 40 g of Eudragit® L and 10 g of HPMC® were co-dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 94%).

Products were tested under the same dissolving conditions as described in Example 1 and the data were as follows:

|          | % cisapride dissolved | |
| Time (hour) | pH = 1.2 | pH = 7.5 |
| --- | --- | --- |
| 1 | 33 | 12 |
| 2 | 56 | 35 |
| 4 | 65 | 35 |
| 8 | 80 | 72 |
| 16 | 81 | 93 |
| 24 | 81 | 96 |

40 g of cisapride, 10 g of Eudragit® L and 40 g of HPMC® were co-dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 97%).

Products were tested under the same dissolving conditions as described in Example 1 and the data were as follows:

|          | % cisapride dissolved | |
| Time (hour) | pH = 1.2 | pH = 7.5 |
| --- | --- | --- |
| 1 | 31 | 25 |
| 2 | 42 | 35 |
| 4 | 57 | 48 |
| 8 | 75 | 68 |
| 16 | 84 | 90 |
| 24 | 84 | 95 |

Example 8

40 g of cisapride, 20 g of Eudragit® L and 20g of HPMC® were co-dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 94%).

Products were tested under the same dissolving conditions as described in Example 1 and the data were as follows:

|          | % cisapride dissolved | |
| Time (hour) | pH = 1.2 | pH = 7.5 |
| --- | --- | --- |
| 1 | 12 | 18 |
| 2 | 16 | 28 |
| 4 | 22 | 45 |
| 8 | 31 | 77 |
| 16 | 41 | 99 |
| 24 | 50 | 100 |

Example 9

40 g of cisapride, 25 g of Eudragit® L and 15 g of HPMC® were dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 95%).

Products were tested under the same dissolving conditions as described in Example 1 and the data were as follows:

|          | % cisapride dissolved | |
| Time (hour) | pH = 1.2 | pH = 7.5 |
| --- | --- | --- |
| 1 | 21 | 11 |
| 2 | 26 | 27 |
| 4 | 34 | 58 |
| 8 | 43 | 97 |
| 16 | 53 | 100 |
| 24 | 59 | 100 |

Example 10

40 g of cisapride, 30 g of Eudragit® L and 20 g of HPMC® were co-dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 96%).

Products were tested under the same dissolving conditions as described in Example 1 and the data were as follows:

|          | % cisapride dissolved | |
| Time (hour) | pH = 1.2 | pH = 7.5 |
| --- | --- | --- |
| 1 | 21 | 11 |
| 2 | 26 | 27 |
| 4 | 34 | 58 |
| 8 | 43 | 97 |
| 16 | 53 | 100 |
| 24 | 59 | 100 |

Example 11

40 g of cisapride, 40 g of HPMCP® (hydroxypropylmethylcellulose, Shin Etsu, Japan) and 20 g of Tween 80 were co-dissolved in a mixture of 550 ml of acetone and 30 ml of water. 60 g of 30–35 mesh sugar-core beads were coated with the above mixture. Upon completion, the beads thus-coated were cured to from drug-core spheres (yield 80%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 11 | 73 |
| 2 | 16 | 81 |
| 4 | 21 | 89 |
| 8 | 26 | 95 |
| 16 | 31 | 98 |
| 24 | 35 | 99 |

Example 12

40 g of cisapride, 40 g of HPMCP® and 20 g of Tween 80 were dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 96%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 25 | 40 |
| 2 | 31 | 68 |
| 4 | 40 | 91 |
| 8 | 52 | 100 |
| 16 | 67 | 100 |
| 24 | 78 | 100 |

Example 13

40 g of cisapride, 40 g of HPMCP® and 2 g of sodium lauryl sulfate were dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 95%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 2 | 23 |
| 2 | 3 | 31 |
| 4 | 5 | 42 |
| 8 | 12 | 58 |
| 16 | 26 | 74 |
| 24 | 34 | 79 |

Example 14

40 g of cisapride, 40 g of HPMCP®, and 16 g of HPMC® were dissolved in a mixture of 250 ml methanol and 250 ml of methylene chloride. 60 g of 30–35 mesh sugar-core beads were coated with the above mixture. Upon completion, the beads thus-coated were cured to from drug-core spheres (yield 96%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 8 | 15 |
| 2 | 12 | 30 |
| 4 | 19 | 58 |
| 8 | 23 | 74 |
| 16 | 28 | 87 |
| 24 | 33 | 89 |

Example 15

40 of cisapride and 40 g of HPMCP® were dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 95%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 1 | 27 |
| 2 | 3 | 37 |
| 4 | 5 | 52 |
| 8 | 12 | 72 |
| 16 | 26 | 89 |
| 24 | 29 | 93 |

Example 16

40 g of cisapride, 40 g of HPMCP®, 10 g of Tween 80 and 8 g of HPMC® were dissolved in a mixture of 250 ml of methanol and 250 ml of methylene chloride. 60 g of 30–35 mesh sugar-core beads were coated with the above mixture. Upon completion, the beads thus-coated were cured to form drug-core spheres (yield 96%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 7 | 14 |
| 2 | 18 | 23 |
| 4 | 56 | 36 |
| 8 | 85 | 56 |
| 16 | 87 | 83 |
| 24 | 87 | 93 |

Example 17

40 g of cisapride, 20 g of HPMCP® and 20 g of HPMC® were dissolved in a mixture of 250 of methanol and 250 ml of methylene chloride. 60 g of 30–35 mesh sugar-core beads were coated with the above mixture. Upon completion, the beads thus-coated were cured to from drug-core spheres (yield 93%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 8 | 30 |
| 2 | 15 | 36 |
| 4 | 23 | 44 |
| 8 | 37 | 57 |
| 16 | 61 | 76 |
| 24 | 80 | 88 |

Example 18

40 g of cisapride, 20 g of HPMCP® and 40 g of HPMC® were dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 94%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 26 | 26 |
| 2 | 31 | 33 |
| 4 | 62 | 47 |
| 8 | 78 | 69 |
| 16 | 79 | 85 |
| 24 | 79 | 90 |

Example 19

40 g of cisapride, 10 g of HPMCP® and 40 g of HPMC® were dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 94%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 38 | 6 |
| 2 | 56 | 12 |
| 4 | 76 | 32 |
| 8 | 82 | 69 |
| 16 | 83 | 92 |
| 24 | 83 | 96 |

Example 20

40 g of cisapride, 40 g of Opadry® (product from Colorcon) and 20 g of Tween 80 were dissolved in a mixture of 250 ml of methanol and 250 ml of methylene chloride. 60 g of 30–35 mesh sugar-core besugar-core beads were coated with the above mixture. Upon completion, the beads thus-coated were cured to from drug-core spheres (yield 96%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 23 | 21 |
| 2 | 29 | 45 |
| 4 | 35 | 81 |
| 8 | 41 | 100 |
| 16 | 48 | 100 |
| 24 | 52 | 100 |

Example 21

Step 1

40 g Eudragit® L30D, 0.47 g of triethyl citrate and 2.33 g of talc were mixed in 17.83 of water and stirred homogeneously. 50 g of the product produced as in Example 10 were coated with the above mixture. Upon completion, the beads thus-coated were cured to form drug-core spheres (yield 97%).

Step 2

40 g of cisapride, 20 g of HPMC® and 20 g of Tween 80 were dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 90%).

Mixed products consisted of 25% each of the product from Example 8 and the product from step 2 of this example as well as 50% of the product of the step 1 of this example were tested under the same dissolving conditions as described in Example 1 and the data wand the data were as follows:

| Time (hour) | % cisapride dissolved | |
| --- | --- | --- |
| | pH = 1.2 | pH = 7.5 |
| 1 | 19 | 7 |
| 2 | 25 | 29 |
| 4 | 27 | 44 |
| 8 | 31 | 72 |
| 16 | 37 | 88 |
| 24 | 41 | 94 |

Example 22

20 g of cisapride, 10 g of Eudragit® L and 10 g of HPMC® were dissolved in a mixture of 125 ml of methanol and 125 ml of methylene chloride. 120 g of 30–35 mesh sugar-core beads were coated with the above mixture. Upon completion, the beads thus-coated were cured to from drug-core spheres. 47.5 g of Eudragit® L, 1.43 g of TEC and 7.13 g talc were mixed in 54.6 ml water to form a solution A. 10 g of cisapride, 5 g of Eudragit® L and 5 g of HPMC® were dissolved in a mixed solvent of 62.5 ml of methanol and 62.5 ml of methylene chloride to form a solution B. 10 g of cisapride, 5 g of HPMC® and 5 g of Tween 80 were dissolved in a mixed solvent of 62.5 ml of methanol and 62.5 ml of methylene to form a solution C. The drug-core bead produced as above were coated sequentially with the above-described solutions A, B and C. Upon completion, the beads thus-coated wethus-coated were cured to form the product (yield 98%).

Products were tested under the same dissolving conditions as described in Example 1 and the data were as follows:

| | % cisapride dissolved | |
|---|---|---|
| Time (hour) | pH = 1.2 | pH = 7.5 |
| 1 | 41 | 52 |
| 2 | 42 | 73 |
| 4 | 44 | 88 |
| 8 | 45 | 96 |
| 16 | 46 | 98 |
| 24 | 46 | 98 |

Example 23

40 g of cisapride, 40 g of HPMCP®, 20 g of Tween 80 and 16 g of HPMC® were dissolved in a mixture of 250 ml of methanol and 250 ml of methylene chloride. 60 g of 30–35 mesh sugar-core beads were coated with the above mixture. Upon completion, the beads thus-coated were cured to from drug-core spheres (yield 95%).

Products were tested under the same dissolving conditions as described in Example 1 and the data were as follows:

| | % cisapride dissolved | |
|---|---|---|
| Time (hour) | pH = 1.2 | pH = 7.5 |
| 1 | 28 | 89 |
| 2 | 40 | 95 |
| 4 | 55 | 96 |
| 8 | 83 | 96 |
| 16 | 82 | 96 |
| 24 | 83 | 99 |

Example 24

40 g of cisapride, 20 g of Eudragit® L, 20 g of HPMC® and 5 g of ethyl cellulose were dissolved in a mixture of 250 ml of methanol and 250 ml of methylene chloride. 60 g of 25–30 mesh sugar-core beads were coated with the above mixture. Upon completion, the beads thus-coated were cured to from drug-core spheres (yield 97%).

Products were tested under the same dissolving conditions as described in Example 1 and the data were as follows:

| | % cisapride dissolved | |
|---|---|---|
| Time (hour) | pH = 1.2 | pH = 7.5 |
| 1 | 8 | 11 |
| 2 | 11 | 20 |
| 4 | 17 | 51 |
| 8 | 30 | 88 |
| 16 | 55 | 100 |
| 24 | 67 | 100 |

Example 25

40 g of cisapride, 20 g of HPMCP®, 20 g of HPMC® and 5 g of ethyl cellulose were dissolved in a mixture of 250 ml of methanol and 250 ml of methylene chloride. 60 g of 25–30 mesh sugar-core beads were coated with the above mixture. Upon completion, the beads thus-coated were cured to from drug-core spheres (yield 91%).

Products were tested under the same dissolving conditions as described in Example 1 and the data were as follows:

| | % cisapride dissolved | |
|---|---|---|
| Time (hour) | pH = 1.2 | pH = 7.5 |
| 1 | 14 | 8 |
| 2 | 19 | 19 |
| 4 | 27 | 58 |
| 8 | 39 | 95 |
| 16 | 57 | 100 |
| 24 | 69 | 100 |

Example 26

40 g of cisapride, 20 g of HPMCP® and 20 g of HPMC® were dissolved in a mixture of 250 ml of methanol and 250 ml of methylene chloride. 60 g of 25-30 mesh sugar-core beads were coated with the above mixture. Upon completion, the beads thus-coated were cured to from drug-core spheres (yield 91%). 13.4 g of Eudragit® L100, 13.4 g of Eudragit® S 100 and 2.67 g of DBP were dissolved in a mixture of 267 ml of acetone and 5.3 ml of water to form a solution A. 19.6 g of cisapride and 9.8 g of HPMC® were dissolved in a mixture of 95 ml of methanol and 95 ml of methylene chloride to form a solution B. The drug-core bead produced as above were coated sequentially with the above-described solutions A and B. Upon completion, the beads thus-coated were cured to form the product (yield 80%).

Products were tested under the same dissolving conditions as described in Example 1 and the data were as follows:

| | % cisapride dissolved | |
|---|---|---|
| Time (hour) | pH = 1.2 | pH = 7.5 |
| 1 | 11 | 24 |
| 2 | 18 | 56 |
| 4 | 29 | 95 |
| 8 | 45 | 97 |
| 16 | 65 | 98 |
| 24 | 71 | 99 |

Example 27

αg of cisapride, 30 g of HPMCP® and 30 g of HPMC® were dissolved in a mixture of 378 ml of methanol and 378 ml of methylene chloride. 60 g of 25–30 mesh sugar-core beads were coated with the above mixture. Upon completion, the beads thus-coated were cured to form drug-core spheres (yield 91%). 15 g of Eudragit® L 100, 15 g of Eudragit® S 100 and 3 g of DBP were dissolved in a mixture of 300 ml of acetone and 6 ml of water to form a solution A. 40 g of cisapride, 20 g of HPMC® and 20 g of HPMCP® were dissolved in a mixture of 252 ml of methanol and 252 ml of methylene chloride to form a solution B. The drug-core beads produced as above were coated sequentially with the above-described solutions A and B. Upon completion, the beads thus-coated were cured to form the product (yield 80%).

Products were tested under the same dissolving conditions as described in Example 1 and the data were as follows:

| Time (hour) | % cisapride dissolved | |
| --- | --- | --- |
| | pH = 1.2 | pH = 7.5 |
| 1 | 9 | 42 |
| 2 | 14 | 83 |
| 4 | 22 | 89 |
| 8 | 30 | 91 |
| 16 | 37 | 92 |
| 24 | 39 | 93 |

The examples provided above are not meant to limit the invention. Many other variations and modifications of the above described embodiments of the present invention would be carried out without departing from the spirit and scope of this invention.

What is claimed is:

1. A bioavailable sustained release cisapride dosage form, comprising a pharmaceutically acceptable substrate coated with at least one layer comprising an effective amount of cisapride and at least one enteric polymer, wherein the enteric polymer is selected from the group consisting of:
   (i) an enteric acrylic polymer;
   (ii) a phthalic acid derivative of vinyl polymer or copolymer; and
   (iii) a phthalic acid derivative of cellulose,
wherein the weight ratio of cisapride to the enteric polymer is between 10:1 and 1:10.

2. A bioavailable sustained release cisapride dosage form according to claim 1, further comprising at least one hydrophobic substance, wherein the hydrophobic substance is selected from the group consisting of:
   (i) an acrylic polymer; and
   (ii) an alkyl cellulose,
wherein the hydrophobic substance based on the cisapride dosage form is between 1% and 30% by weight.

3. A bioavailable sustained release cisapride dosage form according to claim 2, further comprising at least one layer of overcoat, wherein the overcoat comprises an effective amount of cisapride and at least one enteric polymer, the enteric polymer in the overcoat being selected from the group consisting of:
   (i) an enteric acrylic polymer;
   (ii) a phthalic acid derivative of vinyl polymer or copolymer; and
   (iii) a phthalic acid derivative of cellulose,
wherein the weight ratio of cisapride to the enteric polymer in the overcoat is between 10:1 and 1:10.

4. A bioavailable sustained release cisapride dosage form according to claim 1, wherein the weight ratio of cisapride to the enteric polymer is between 5:1 and 1:5.

5. A bioavailable sustained release cisapride dosage form according to claim 4, wherein the weight ratio of cisapride to the enteric polymer is between 2:1 and 1:2.

6. A bioavailable sustained release cisapride dosage form according to claim 2, which comprises 1% to 20% by weight of the hydrophobic substance based on the cisapride dosage form.

7. A bioavailable sustained release cisapride dosage form according to claim 6, which comprises 1% to 10% by weight of the hydrophobic substance based on the cisapride dosage form.

8. A bioavailable sustained release cisapride dosage form according to claim 3, wherein the weight ratio of cisapride to the enteric polymer in the overcoat is between 5:1 and 1:5.

9. A bioavailable sustained release cisapride dosage form according to claim 8, herein the weight ratio of cisapride to the enteric polymer in the overcoat is between 2:1 and 1:2.

10. A bioavailable sustained release cisapride dosage form according to claim 1 for use in once-a-day oral administration.

11. A bioavailable sustained release cisapride dosage form according to claim 2 for use in once-a-day oral administration.

12. A bioavailable sustained release cisapride dosage form according to claim 3 for use in once-a-day oral administration.

13. A bioavailable sustained release cisapride dosage form according to claim 1 for use in twice-a-day oral administration.

14. A bioavailable sustained release cisapride dosage form according to claim 2 for use in twice-a-day oral administration.

15. A bioavailable sustained release cisapride dosage form according to claim 3 for use in twice-a-day oral administration.

16. A bioavailable sustained release cisapride dosage form according to claim 1, wherein the enteric acrylic polymer is a copolymer of methyl methacrylate and methacrylic acid.

17. A bioavailable sustained release cisapride dosage form according to claim 2, wherein the enteric acrylic polymer is a copolymer of methyl methacrylate and methacrylic acid.

18. A bioavailable sustained release cisapride dosage form according to claim 3, wherein the enteric acrylic polymer in the overcoat is a copolymer of methyl methacrylate and methacrylic acid.

19. A bioavailable sustained release cisapride dosage form according to claim 1, wherein the phthalic acid derivative is a hydroxypropylmethylcellulose phthalate or cellulose phthalate acetate.

20. A bioavailable sustained release cisapride dosage form according to claim 2, wherein the phthalic acid derivative is a hydroxypropylmethylcellulose phthalate or cellulose phthalate acetate.

21. A bioavailable sustained release cisapride dosage form according to claim 3, wherein the phthalic acid derivative in the overcoat is a hydroxypropylmethylcellulose phthalate or cellulose phthalate acetate.

22. A pharmaceutical composition which comprises a plurality of bioavailable sustained release cisapride dosage forms according to claim 1.

23. A pharmaceutical composition which comprises a plurality of bioavailable sustained release cisapride dosage forms according to claim 2.

24. A pharmaceutical composition which comprises a plurality of sustained release cisapride dosage forms including at least a first bioavailable sustained release cisapride dosage form according to claim 1 and at least a second bioavailable sustained release cisapride dosage form comprising a pharmaceutically acceptable substrate coated with at least one layer comprising an effective amount of cisapride and at least one enteric polymer wherein the enteric polymer is selected from the group consisting of: (i) an enteric acrylic polymer; (ii) a phthalic acid derivative of vinyl polymer or copolymer; and (iii) a phthalic acid derivative of cellulose, wherein the weight ratio of cisapride to the enteric polymer is between 10:1 and 1:10, and at least one hydrophobic substance, wherein the hydrophobic substance is selected from the group consisting of: (i) an acrylic polymer; and (ii) an alkyl cellulose, wherein the hydrophobic substance based on the cisapride dosage form is between 1% and 30% by weight.

25. A pharmaceutical composition which comprises a plurality of bioavailable sustained release cisapride dosage forms according to claim 3.

* * * * *

UNITED STATES PATENT AND TRADEMARK OFFICE
CERTIFICATE OF CORRECTION

PATENT NO. : 6,221,396 B1
DATED : April 24, 2001
INVENTOR(S) : Shouchung Chao, et al.

It is certified that error appears in the above-identified patent and that said Letters Patent is hereby corrected as shown below:

<u>Title page,</u>
Item [30], "CN" should read -- Taiwan --.

Signed and Sealed this

Thirtieth Day of October, 2001

Attest:

*Nicholas P. Godici*

NICHOLAS P. GODICI
*Acting Director of the United States Patent and Trademark Office*

*Attesting Officer*